United States Patent [19]

Morse et al.

[11] Patent Number: 5,318,524

[45] Date of Patent: Jun. 7, 1994

[54] FIBRIN SEALANT DELIVERY KIT

[75] Inventors: Brenda S. Morse, Chamblee; A. Denise Turner, Dunwoody; Robert T. McNally, Marietta, all of Ga.

[73] Assignee: CryoLife, Inc., Marietta, Ga.

[21] Appl. No.: 844,497

[22] Filed: Mar. 2, 1992

Related U.S. Application Data

[63] Continuation-in-part of Ser. No. 460,379, Jan. 3, 1990, Pat. No. 5,219,328.

[51] Int. Cl.$^5$ .............................................. A61M 37/00
[52] U.S. Cl. ........................................ 604/82; 604/92; 604/416; 606/214
[58] Field of Search ................... 128/DIG. 22; 606/3, 606/8, 11, 213-215; 604/46, 49, 56, 82-92, 416, 290; 602/48-50

[56] References Cited

U.S. PATENT DOCUMENTS

| | | | |
|---|---|---|---|
| 2,193,717 | 3/1940 | Faust | 128/DIG. 22 |
| 2,492,458 | 12/1949 | Bering . | |
| 2,533,004 | 12/1950 | Ferry et al. . | |
| 3,723,244 | 3/1973 | Breillatt, Jr. . | |
| 4,265,233 | 5/1981 | Sugitachi et al. . | |
| 4,359,049 | 11/1982 | Redl et al. . | |
| 4,359,463 | 11/1982 | Rock . | |
| 4,377,572 | 3/1983 | Schwarz et al. . | |
| 4,427,651 | 1/1984 | Stroetmann . | |
| 4,442,655 | 4/1984 | Stroetmann . | |
| 4,453,939 | 6/1984 | Zimmerman et al. . | |
| 4,627,879 | 12/1986 | Rose et al. . | |
| 4,631,055 | 12/1986 | Redl et al. . | |
| 4,655,211 | 4/1987 | Sakamoto et al. . | |
| 4,668,621 | 5/1987 | Doellgast | 435/13 |
| 4,696,812 | 9/1987 | Silbering et al. . | |
| 4,735,616 | 4/1988 | Eibl et al. . | |
| 4,874,368 | 10/1989 | Miller et al. | 604/82 |
| 4,902,281 | 2/1990 | Avoy . | |
| 4,909,251 | 3/1990 | Seelich | 606/213 |
| 5,030,215 | 7/1991 | Morse et al. | 604/416 |
| 5,104,375 | 4/1992 | Wolf et al. | 604/82 |
| 5,116,315 | 5/1992 | Capozzi et al. | 604/82 |
| 5,226,877 | 7/1993 | Epstein | 606/214 |

FOREIGN PATENT DOCUMENTS

| | | |
|---|---|---|
| 0172710 | 2/1986 | European Pat. Off. . |
| 0221700 | 5/1987 | European Pat. Off. . |
| 0253198 | 1/1988 | European Pat. Off. . |
| 3622642A1 | 1/1988 | Fed. Rep. of Germany . |
| 2422407 | 11/1979 | France . |
| 2042556 | 9/1990 | United Kingdom . |

OTHER PUBLICATIONS

Nowotny et al, "Mechanical Properties of Fibrinogen-Adhesive Material", Adv. Biomaterials, 3:677-682 (1982).

Redl et al, "Background and Methods of Fibrin Sealing", Adv. Biomaterials, 3:669-676 (1982).

Dresdale et al., Hemostatic effectiveness of Fibrin Glue Derived from Single-Donor Fres Frozen Plasma, Ann. Thorac. Surg., 40:385 (1985).

Lupinetti et al., Cryoprecipitate-topical thrombin gel: Initial experience in patients undergoing cardiac operations, J. Thorac. Cardiovasc. Surg., 90:502 (1985).

Carr et al, Influence of Ca2+ on the Structure of Reptilase-derived and Thrombin-derived fibrin gels, Biochem. J., 239:513 (1986).

(List continued on next page.)

Primary Examiner—C. Fred Rosenbaum
Assistant Examiner—Mark Bockelman
Attorney, Agent, or Firm—Nixon & Vanderhye

[57] ABSTRACT

The present invention relates to a method for the formulation of fibrin sealant in a single delivery system. The method involves mixing a fibrinogen/Factor XIII precipitate solution with thrombin under conditions such that thrombin clotting activity is inhibited and said mixture is applied to a body site under conditions which activate the thrombin to convert fibrinogen into fibrin sealant. A single device, syringe or container, can be used to apply the fibrin sealant formulation.

8 Claims, No Drawings

OTHER PUBLICATIONS

Kaminski et al., Studies on the Mechanism of Thrombin, J. Biol. Chem. 258:10530 (1983).

Turner et al, Photochemical Activation of Acylated-Thrombin, J. Am. Chem. Soc. 109:1274–1275 (1987).

Turner et al, Photoreactivation of Irreversibly Inhibited Serine Proteases, J. Am. Chem. Soc. 110:244–250 (1988).

Porter et al, Acyl Thrombin Photochemistry: Kinetics for Deacylation of Enzyme Cinnamate Geometric Isomers, J. Am. Chem. Soc. 111:7616–7618 (1989).

Laki, The Polymerization of Proteins: the Action of Thrombin on Fibrinogen, Arch Biochem, Biophys., 32:317–324 (1951).

Haberli et al, (1987) Biopolymers 26:27–43.

David E. Metzler, "Biochemistry, The Chemical Reactions of Living Cells", Academic Press, Inc. N.Y. 1977, pp. 330–331.

Arthur C. Guyton, "Physiology of the Human Body", W. B. Saunders Company, Philadelphia 1979 pp. 69–75.

FIBRIN SEALANT DELIVERY KIT

This invention was made with Government support under Grant No. 1-R43-HL46096-01 awarded by the National Institutes of Health. The Government has certain rights in the invention.

This is a continuation-in-part application of Ser. No. 07/460,379 filed on Jan. 3, 1990, now U.S. Pat. No. 5,219,328, which is hereby incorporated herein in its entirity.

BACKGROUND OF THE INVENTION

1. Technical Field

The present invention relates to a method of fibrin sealant preparation and delivery, which permits use of a single delivery device. The method may be used for autologous, single-donor, pooled-donor or cell culture-derived fibrin sealant for various human and veterinary surgical procedures. The invention further relates to a kit suitable for use in such a method.

2. BACKGROUND INFORMATION

The blood coagulation system is a complex series of proteins and factors which are activated sequentially to produce a fibrin gel or clot. In the final stages of the process, fibrinogen is cleaved by thrombin to generate fibrin monomer, which rapidly polymerizes and is cross-linked by activated Factor XIII to form a fibrin matrix.

Preparations of human coagulation factors, including fibrinogen and thrombin, have been used extensively in surgery over the last ten years (Schlag et al (eds), Fibrin Sealant in Operative Medicine, vol 1-7, Springer-Verlag, Heidelberg). These biological fibrin sealants promote hemostasis and wound healing by sealing leakage from tissues, sutures, staples, and prostheses, and are particularly useful during open heart surgery in heparinized patients. The sealants also have use as an adhesive for the bonding of tissues and they reduce the amount of blood required for transfusions by controlling intraoperative bleeding. Their effectiveness is reflected in the extensive range of surgical applications for which they have been used, including cardiovascular surgery, plastic surgery, orthopedics, urology, obstetrics and gynecology, dentistry, maxillofacial and ophthalmic surgery.

Fibrin sealant products prepared from pooled human plasma fibrinogen/Factor XIII are available commercially in Europe (Tissucol/Tisseel, Immuno AG, Vienna, Austria and Beriplast P, Hoechst, West Germany) but such products have not received U.S. Food and Drug Administration approval. As an alternative, some hospitals are preparing fibrin sealant in-house using the patient's own blood (autologous) or single-donor (homologous) plasma as a source of fibrinogen and Factor XIII.

The plasma fibrinogen/Factor XIII component of fibrin sealant is typically prepared by freezing plasma at a temperature below $-20°$ C. overnight, slowly thawing the material at $0°-4°$ C., centrifuging, and transferring the cryoprecipitate to a syringe or spray container (Dresdale et al, Ann. Thorac. Surg. 40:385 1985; and U.S. Pat. No. 4,627,879). The thrombin component, usually purified from bovine plasma, can be obtained commercially and is typically prepared in a separate syringe or spray container. In use, the two solutions are delivered simultaneously or alternately to generate fibrin sealant at the site of the wound; alternatively, the sealant is applied to a collagen matrix (e.g. Gelfoam or Avitene) and then pressed against the site (Lupinetti et al, J. Thorac. Cardiovasc. Surg. 90:502 1985; and U.S. Pat. No. 4,453,939).

The use of fibrin sealant in surgery has been limited by problems associated with mixing and delivery of the sealant to the wound. Generation of fibrin sealant at the wound site is currently achieved using a two syringe or spray container system to prevent premature mixing and clotting of the components. Such two syringe systems are, however, unsatisfactory due to the awkwardness of filling and manipulating the delivery devices at the wound site. In addition, the syringe system is accompanied by problems of inadequate mixing of the two solutions, resulting in the formation of a weak clot. Alternatively, the two syringes can be placed into a holder designed such that the solutions are permitted to mix before entering the needle (U.S. Pat. Nos. 4,735,616, 4,359,049, and 4,631,055). The mixing chamber directs the flow of the separate components through two narrow channels and forces mixing at the top of the outflow needle. Although the strength of the clot obtained using this method is reproducible, the needle frequently clogs and must repeatedly be replaced.

In view of the problems inherent in the methodologies currently available for delivering fibrin sealant, the need for a simple, reproducible technique is clear. Such a technique must be convenient to use and must result in the formation, at a specific site, of a clot of appropriate strength. Such a delivery technique is provided by the invention disclosed herein.

SUMMARY OF THE INVENTION

It is a general object of the present invention to provide a method of forming a fibrin sealant from blood coagulation components that overcomes the problems associated with methods known in the art.

It is a specific object of the invention to provide a method of delivering fibrin sealant to a wound site, in which method a fibrinogen/Factor XIII-enriched precipitate (or a fibrinogen/Factor XIII mixture) and thrombin are mixed together under conditions such that clotting is prevented until such time as sealant formation is desired.

It is another object of the present invention to provide means of reversibly inactivating thrombin and subsequently restoring activity which can be used to prevent premature clot formation.

It is a further object of the invention to provide a kit suitable for use in the abovedescribed method.

A more complete appreciation of the present invention and the advantages thereof will be readily understood by one skilled in the art from a reading of the description that follows.

In one embodiment, the present invention relates to a method of effecting the formation of fibrin sealant at a body site. The method comprises: i) mixing, in a container means, an aqueous solution comprising fibrinogen, Factor XIII and mature thrombin under conditions such that thrombin clotting activity is inhibited; and ii) applying a preparation resulting from step (i) to the body site under conditions such that thrombin clotting activity is restored and the fibrin sealant is formed.

In another embodiment, the present invention relates to a method of effecting the formation of fibrin sealant at a body site comprising: i) forming a suspension comprising a first phase which comprises fibrinogen and Factor XIII and a second phase which comprises thrombin, and ii) applying the suspension to the body site under conditions such that mixing of the fibrinogen, Factor XIII and thrombin is effected so that the fibrin sealant is formed.

In a further embodiment, the present invention relates to a kit for use in the preparation of a fibrin sealant. The kit includes an applicator comprising: i) a container means having disposed therein a solution comprising fibrinogen, Factor XIII and mature thrombin; and ii) an outlet means operably connected to said container means.

DETAILED DESCRIPTION OF INVENTION

The present invention relates to a method of delivering the components of a fibrin sealant (mature thrombin (as opposed to prothrombin) and the plasma-derived fibrinogen/Factor XIII precipitate) to a body site in a manner such that clot formation is effected, and to a kit suitable for use in such a method. (The term "body site" as used herein includes the tissue in the area of a wound or incision as well as implantable tissues or components to be inserted into the area, e.g., vascular prostheses, bone or collagen pads.) In the description that follows, it will be appreciated that a combination of isolated forms of fibrinogen and Factor XIII can be used in place of the plasmaderived precipitate.

In the method of the present invention, a fibrinogen/Factor XIII-enriched precipitate and mature thrombin are mixed together under conditions such that thrombin and/or Factor XIII are/is inactivated (or under conditions such that thrombin is present in an active form but is rendered unavailable, as in the calcium depletion embodiment described below) and clotting thereby prevented. The mixture is then delivered to the body site under conditions such that the enzyme activity is restored (or thrombin availability restored).

In one embodiment, the mixture of thrombin and fibrinogen/Factor XIII precipitate is prepared in a low pH buffer (the clotting of fibrinogen by thrombin being inhibited by low pH (less than 5.5)). In this embodiment, thrombin activity is restored and clotting rapidly initiated upon neutralization of the mixture with a pharmaceutically acceptable buffer, or alternatively, upon contact of the mixture with the patient's own body fluids. In this embodiment, the fibrinogen/Factor XIII precipitate can be prepared at a low pH or, alternatively, a low pH buffer can be used to dissolve the plasma precipitate and the lyophilized thrombin. In either case, the mixture can be transferred to a delivery container (such as a spray bottle or syringe) and applied to the body site directly, if conditions are such that the patient's body fluids are sufficient to increase the pH to a point where clotting occurs. Where conditions are such that the patient's body fluids are not sufficient to raise the pH of the precipitate/thrombin mixture to a point where thrombin activity is restored, a delivery device can be used that is designed such that, as the acidic mixture passes out of the device, it is contacted with buffer salts coated on an interior portion of the device. The buffer salts are selected such that when contact is made with the acidic mixture, dissolution occurs with the result that the pH is raised to a point where clotting takes place. For example, a syringe can be used as the delivery device (applicator), where the syringe is fitted with a disposable tip, the interior surface of which is coated with appropriate buffer salts. As the acidic mixture passes through the coated tip, the buffer (in the form, for example, of crystals or a gel) neutralizes the acidic mixture, thus restoring thrombin activity and effecting the formation of a clot at the desired site. Should clot formation occur in the tip, the tip can simply be removed and a new coated tip attached.

In another embodiment, the fibrinogen and Factor XIII precipitate/thrombin mixture can be prepared in a buffer that is depleted of calcium. Rapid clot formation requires the presence of calcium ions; thus, if the calcium is removed, fibrin polymerization is inhibited (see Carr et al Biochem J. (1986) 239:513; Kaminski et al J. Biol. Chem (1983) 258:10530; Kanaide et al (1982) 13:229). Calcium chelators (compounds such as sodium citrate or ethylenediaminetetraacetic acid, which tightly bind calcium and make it inaccessible) can be added to the solution used to precipitate the fibrinogen and Factor XIII and/or the dissolving buffer. To restore activity, the container (for example, a syringe) can be attached to a disposable sterile tip, the interior surface of which is coated internally with sufficient calcium salt to saturate the chelator. As the free calcium concentration increases upon passage of the mixture through the tip, clotting is effected at the body site.

In a further embodiment, the clotting activity of thrombin, in the precipitate/thrombin mixture, can be inhibited using a photosensitive inhibitor. For example, light sensitive cinnamoyl derivatives can be used to inactivate thrombin, at room temperature in the absence of light, for more than 26 hours (Turner et al J. Am. Chem. Soc. 109: 1274–1275 (1987); Turner et al J. Am. Chem. Soc. 110: 244–250 (1988)). These same thrombin inhibitor complexes can generate active thrombin within 1–2 seconds of irradiation (low intensity). These inhibitors are known to form acyl-enzyme complexes involving the active site serine hydroxyl (SER 195). Upon irradiation, the cinnamoyl derivative undergoes photoisomerization to release coumarin and regenerate the active serine hydroxyl. Since coumarin derivatives are not good thrombin inhibitors, this photocyclization reaction effectively removes inhibitor from the enzyme solution. Thus, a solution of the fibrinogen/Factor XIII-enriched precipitate can be mixed with lyophilized inhibitor:thrombin complex in a dark environment (such as an opaque or colored syringe or container) and delivered to the wound site. Activation of the enzyme and thus clot formation occurs upon delivery to the wound due to the exposure of the solution to normal room light. Alternatively, activation can be controlled by a light source, for example, one built directly into the applicator, so that variations in lighting conditions will not result in variable clotting times.

Preferably, the clotting activity of thrombin, in the precipitate/thrombin mixture is inhibited by the use of a photosensitive inhibitor in combination with an irreversible inhibitor. Such "doubly-inhibited" thrombin offers several advantages including increased stability of the double inhibitor:thrombin complex and fibrinogen/Factor XIII precipitate which reduces premature clot formation during long term storage as well as during use. The doubly inhibited thrombin also provides for increased control of clot activation, increased clot strength and increased time for mixing with additives (such as, for example, bone granules, antibiotics or growth factors).

For example, thrombin activity can be inhibited by the use of the photosensitive inhibitor 4-amidino-phenyl-2-hydroxy-4-diethylamino-alpha-methylcinnamate hydrochloride, "I-1" and the irreversible inhibitor D- phenylalanyl-L-prolyl-L-arginine chloromethyl ketone, "PPACK". I-1 inhibits approximately 99% of the thrombin activity, however, the residual 1% activity can not be reduced by additional I-1. This residual activity, which is sufficient to cause clotting after 15-20 minutes in the absence of light, can be reduced by titrated by the addition of the second inhibitor ("PPACK" in the present example). In the absence of activating irradiation (light of approximately 360 nm as provided by a Caulk UV Polymerization Unit), the doubly inhibited thrombin solution is subsequently added to the fibrinogen component and stored frozen, lyophilized or used within hours. Fibrin sealant prepared from this double inhibitor:thrombin complex and fibrinogen/Factor XIII precipitate can be maintained in the dark without clotting for over 2 hours. When the fibrin sealant is needed, the mixture can be dispensed onto the wound site or appropriate delivery container (such as a spray bottle or syringe) and activated by light to clot in less than 1-2 minutes.

Thrombin inhibited by the combination of such inhibitors may be useful for other applications. For example, the double inhibitor:thrombin complex can be used in situations requiring careful control of clotting activity or when thrombin is used alone to stop bleeding. In addition, the inhibited thrombin can be used to localize clotting activity (for example, eye surgery). The inhibited thrombin may also be used with other components or in other forms (for example, with gel matrix or on solid support) to improve handling of delivery to the wound site.

In yet another embodiment, premature clot formation can be prevented prior to delivery of the fibrinogen and Factor XIII/thrombin mixture by physically separating the thrombin from the fibrinogen/Factor XIII precipitate. In this embodiment, physical separation is effected using a two-phase system. Liquids suitable for use in this embodiment are non-miscible and readily separable into two phases. The two phases are mixed into a suspension before each application and delivered to the wound. Where conditions are such that the patient's body fluids extract the soluble component of the nonaqueous phase, mixing occurs at the body site and clotting is thus initiated. If conditions will not elicit proper mixing of components, a delivery device can be used that is designed such that, as the suspension passes out of the device, it is contacted with a solubilizing agent coated on an interior portion of the device. The solubilizing agent is selected such that when contact is made with the suspension, dissolution occurs with the result that mixing occurs to a degree where clotting takes place. For example, a syringe is fitted with a disposable tip, the interior surface of which is coated with an appropriate phase transfer agent(s). As the suspension passes through the coated tip, the phase transfer agent (in the form, for example, of crystals) assists in the mixing process, thus allowing clot formation. Should clot formation occur in the tip, the tip can simply be removed and a new coated tip attached.

The present invention also relates to a kit suitable for use in the above-described method of delivering fibrin sealant components to a wound site. In a preferred embodiment, the kit includes an applicator designed so as to permit mixing of the fibrinogen/Factor XIII precipitate and thrombin in a single system. The applicator can be one that permits the application at the body site of, for example, a film, or a thin line of the components of fibrin sealant. Alternatively, a pump or aerosol spray applicator can be used.

As suggested above, the applicator can, for example, take the form of a glass or plastic syringe with disposable tips. The shape of the tip will determine the form in which the components are delivered. A tip with a flat, broad end can be used to deliver a thin wide streak of fibrin sealant whereas a narrow tubular end can be used to deliver a round thread of sealant. Applying pressure to force the mixture through a tip constricted with, for example, a mesh screen can be used to produce a spray, resulting in a fine glaze of fibrin sealant. In another embodiment, particularly suitable for use with the above-described photosensitive thrombin inhibitor, the applicator can take the form of a pump or aerosol spray device having a built-in light source situated such that, as the sealant components exit the device, they are irradiated with the light. The wavelength of light used would depend on the photosensitizer.

The kit can be structured so as to include individual storage containers for the separate fibrin sealant components. The kit can also include one or more other storage containers disposed within which are any necessary reagents, including solvents, buffers, etc.

The present invention will be understood in greater detail by reference to the following nonlimiting Examples.

EXAMPLES

Example 1

A precipitate containing fibrinogen and Factor XIII was prepared as follows:

Four hundred fifty microliters of a stock 1 M zinc sulfate solution were added to 5 ml of anticoagulated (citrate phosphate dextrose adenine (CPDA-1)) human plasma. The solution was mixed well without vortexing and centrifuged at 2,000 to 9,000 g for 5 minutes. The supernatant was decanted and discarded.

Inhibition of clotting and reactivation was achieved by any of the following methods:

A. Acid Inhibition—Lyophilized bovine thrombin was dissolved in citrate buffer (500 mM citric acid, 150 mM NaCl, and 20 mM EACA, pH 4.5) to a final concentration of 100 U/ml. Precipitated fibrinogen was dissolved in Tris buffer (50 mM Tris, 250 mM sodium citrate, 150 mM sodium chloride, 50 mM Arginine (Arg), and 20 mM $\epsilon$-amino-caproic acid (EACA), pH 7.4) to a concentration of approximately 15.0 mg/ml. This fibrinogen stock was then diluted 25-fold in citrate buffer. The clotting time for 200 microliters of this fibrinogen solution plus 100 microliters thrombin exceeded 90 seconds in a Becton Dickinson BBL Fibrosystem fibrometer under standard conditions indicating no clot formation. Addition of 70 microliters of 1N sodium hydroxide resulted in clot formation in 3.8 seconds (average of 10 samples).

The following procedures can be used for application to a wound site:

Where body fluids are sufficient to neutralize the acidic mixture of precipitate and thrombin, the mixture can be applied directly to the wound site. Alternatively, the delivery device can be connected to disposable tips coated internally with a neutralizing salt or gel (e.g. Tris). Neutralization of the acidic solution by the buffer salts activates thrombin and restores clotting activity.

B. Chelator Inhibition—Precipitated fibrinogen and lyophilized bovine thrombin were dissolved in Tris buffer (50 mM Tris, 250 mM sodium citrate, 150 mM sodium chloride, 50 mM Arg, and 20 mM EACA, pH 7.4) to a concentration of approximately 15.0 mg/ml and 100 U/ml, respectively. The fibrinogen stock solution was then diluted 25-fold in Tris buffer containing 500 mM sodium citrate. The clotting time for 200 microliters of this fibrinogen solution plus 100 microliters thrombin exceeded 90 seconds in a Becton Dickinson BBL fibrosystem fibrometer under standard conditions. Addition of 50 microliters of a 1M $CaCl_2$ solution resulted in clot formation in 1.8 seconds (average of 10 samples).

The following procedure can be used for application to a wound site:

The delivery device is connected to disposable tips coated internally with a calcium salt or gel. As the mixture passes through the tip, the molar excess of calcium saturates the chelator and clotting is thereby promoted.

C. Photosensitive Inhibition—In the absence of light, a 5 to 20-fold excess of 4-amidino-phenyl-2-hydroxy-4-diethylamino-alpha-methylcinnamate hydrochloride (Porter et al, J. Amer. Chem. Soc. 111:7616 (1989)) was added to thrombin in buffer (approximately 100 U/ml in 50 mM Tris, 250 mM sodium chloride, 250 mM sodium citrate, 20 mM EACA, 50 mM arginine (or urea), pH 7.4, final methanol concentration <10%). The inhibition was allowed to proceed for at least 1 hour at room temperature.

A minimal quantity of this solution was used to dissolve the precipitated fibrinogen/Factor XIII. This sealant required approximately 2 to 3 minutes illumination under standard operating lights to clot completely, whereas a sample mixture kept in the dark did not clot after 90 min.

The following procedures can be used for application to a wound site:

The photosensitive inhibitor-thrombin complex can be mixed with the precipitated fibrinogen/Factor XIII in a colored delivery device that does not transmit light of the activating wavelengths. Delivery of the mixture to an illuminated wound site results in clot formation.

D. Two Phase Suspension—Lyophilized bovine thrombin is dissolved in an emulsifying agent to a final concentration of about 100 U/ml. Precipitated fibrinogen/Factor XIII is dissolved in a minimal volume of buffer (50 mM Tris, 150 mM sodium chloride, 250 mM sodium citrate, 20 mM EACA, 50mM Arg, pH 7.4). A suspension of the immiscible liquids is formed. On a wound surface, body fluids may be sufficient to dissolve both components and promote proper mixing and clot formation.

Example 2

A fibrin sealant was prepared using the two enzyme inhibitors as follows. All inactivation and transfer steps were performed in the absence of activating light (366 nm), using a dark room illuminated by a red light.

Thrombin was inactivated sequentially using 1) the light sensitive inhibitor 4-amidinophenyl-2-hydroxy-4-diethylamino-alpha-methylcinnamate hydrochloride and 2) D-Phenylalanyl-L-prolyl-L-arginine Chloromethyl Ketone, PPACK. Bovine thrombin (0.1 ml of 1,000 units/ml Armour Thrombinar) was mixed with 0.8 ml of 50 mM tris buffer, pH 7.3, and 0.1 ml of 31.25 µg/ml inhibitor in 2.5% ethanol, 50 mM tris, pH 7.3. The solution was incubated at room temperature for 2 hours.

Residual thrombin activity of the thrombin:inhibitor-1 complex (approximately 1% original activity) was inactivated by titration with PPACK until residual activity was such that the resulting fibrin sealant could be maintained in the dark for 2–4 hours without premature clotting. The above solution (0.1 ml) was mixed with 0.01 ml of 2.5 µg/ml PPACK at room temperature and thrombin activity of the thrombin:inhibitor-2 was negligible within minutes.

Fibrin sealant was prepared by mixing 1 ml fibrinogen stock (e.g. single unit human cryoprecipitate) with 0.1 ml of the thrombin:inhibitor-2 in the absence of activating light (e.g. opaque container) and transferred to an amber syringe or spray container for delivery.

Clotting activity was easily controlled using light. In the absence of activating light, the mixture was stable for at least 2 hours at room temperature before clotting occurred. A 20 second pulse of light (that is, light of 360 nm, by Caulk MAX polymerization unit) at a distance of less than 5 cm from the dispensed solution resulted in clotting within seconds.

The entire contents of each of the references cited above are hereby incorporated by reference.

While the present invention has been described in some detail for purposes of clarity and understanding, it will be clear to one skilled in the art from a reading of this disclosure that various changes can be made in form and detail without departing from the true scope of the invention.

What is claimed is:

1. An applicator for use in the preparation of a fibrin sealant comprising a container means and an outlet means operably connected thereto, said container means having disposed therewithin a solution consisting essentially of fibrinogen, Factor XIII, mature thrombin and an agent that inhibits the clotting activity of said mature thrombin.

2. A kit for use in the preparation of a fibrin sealant comprising an applicator that comprises:
   i) a container means having disposed therewithin a solution comprising fibrinogen, Factor XIII, mature thrombin and a calcium chelator; and
   ii) an outlet means operably connected to said container means, wherein said outlet means has a calcium salt disposed therewithin.

3. A kit for use in the preparation of a fibrin sealant comprising an applicator that comprises:
   i) a container means having disposed therewithin a solution comprising fibrinogen, Factor XIII and mature thrombin, wherein said solution has a pH of less than about 5.5; and
   ii) an outlet means operably connected to said container means, wherein said outlet means has a neutralizing buffer salt disposed therewithin.

4. A kit for use in the preparation of a fibrin sealant comprising an applicator that comprises:
   i) a container means having disposed therewithin a solution comprising fibrinogen, Factor XIII, mature thrombin and a photosensitive inhibitor of thrombin clotting activity; and
   ii) an outlet means operably connected to said container means,
   wherein said container means and said outlet means are constructed of a material that does not transmit light of a wavelength to which said inhibitor is sensitive.

5. The kit according to claim 4 wherein said outlet means is attached to a source of light that, when activated, emits light at a wavelength that inactivates said photosensitive inhibitor.

6. The kit according to claim 4 wherein said solution further comprises a second inhibitor of thrombin clotting activity.

7. The kit according to claim 6 wherein said second inhibitor is D-phenylalanyl-L-prolyl-L-arginine chloromethyl ketone.

8. The kit according to claim 4 wherein said photosensitive inhibitor is a cinnamoyl derivative.

* * * * *